(12) United States Patent
Murzynski

(10) Patent No.: US 8,205,623 B2
(45) Date of Patent: Jun. 26, 2012

(54) COATINGS FOR PERSONAL GROOMING APPARATUS CONTAINING CALCIUM CARBONATE DERIVED FROM MOLLUSK SHELLS OR PEARLS

(75) Inventor: Maciej Murzynski, Verona, WI (US)

(73) Assignee: Rovcal, Inc., Madison, WI (US)

( * ) Notice: Subject to any disclaimer, the term of this patent is extended or adjusted under 35 U.S.C. 154(b) by 10 days.

(21) Appl. No.: 12/754,058

(22) Filed: Apr. 5, 2010

(65) Prior Publication Data

US 2011/0240055 A1 Oct. 6, 2011

(51) Int. Cl.
| | | |
|---|---|---|
| A45D 24/00 | (2006.01) | |
| A45D 44/00 | (2006.01) | |
| C08L 89/04 | (2006.01) | |
| C08L 89/00 | (2006.01) | |
| C09D 189/04 | (2006.01) | |
| C09D 189/00 | (2006.01) | |
| C09J 189/04 | (2006.01) | |
| C09J 189/00 | (2006.01) | |
| A61K 8/02 | (2006.01) | |
| A61K 8/00 | (2006.01) | |
| A61K 8/18 | (2006.01) | |
| A61Q 5/04 | (2006.01) | |
| A61K 8/72 | (2006.01) | |
| A61K 33/00 | (2006.01) | |
| A61Q 5/00 | (2006.01) | |
| A61Q 7/00 | (2006.01) | |
| A01N 59/00 | (2006.01) | |

(52) U.S. Cl. ............... 132/163; 132/333; 106/124.4; 106/157.2; 424/401; 424/70.2; 424/70.11; 424/715

(58) Field of Classification Search ............ 132/163, 132/202, 210, 212, 162, 221, 245, 269, 73, 132/75.6, 76.4, 285, 319, 320, 333, 321, 132/273, 276; 424/484, 70.1, 70.12, 78.03, 424/547, 401, 687, 70.2, 70.11, 715; 514/63; 427/402; 119/234, 244; 452/12; 106/424, 106/464, 124.4, 157.2, 286.6, 415

See application file for complete search history.

(56) References Cited

U.S. PATENT DOCUMENTS

| | | | | |
|---|---|---|---|---|
| 4,343,910 | A * | 8/1982 | Busch et al. ............... | 521/82 |
| 4,381,792 | A * | 5/1983 | Busch et al. ............ | 132/75.6 |
| 4,393,045 | A * | 7/1983 | Henderson et al. ......... | 424/547 |
| 5,084,279 | A * | 1/1992 | Kato et al. ................ | 424/547 |
| 5,470,323 | A * | 11/1995 | Smith et al. ............... | 604/289 |

(Continued)

FOREIGN PATENT DOCUMENTS

EP 2204104 A1 7/2010

(Continued)

OTHER PUBLICATIONS www.remingtonproducts.com (pearl styling wand).*

(Continued)

*Primary Examiner* — Todd Manahan
*Assistant Examiner* — Vanitha Elgart
(74) *Attorney, Agent, or Firm* — Armstrong Teasdale LLP

(57) ABSTRACT

This disclosure relates to personal grooming apparatus that include coatings on the surface thereof that incorporate calcium carbonate derived from the shell of a mollusk and/or from a mollusk pearl. Other aspects of the present disclosure relate to methods for producing such apparatus, and methods of grooming the hair or skin of an individual.

29 Claims, 5 Drawing Sheets

U.S. PATENT DOCUMENTS

| | | | |
|---|---|---|---|
| 5,773,034 A * | 6/1998 | Camprasse et al. | 424/547 |
| 5,807,554 A * | 9/1998 | Yng-Wong | 424/728 |
| 5,941,253 A * | 8/1999 | Kaizuka | 132/232 |
| 5,968,772 A * | 10/1999 | Matsushiro | 435/69.1 |
| 6,039,054 A * | 3/2000 | Park et al. | 132/321 |
| 6,251,438 B1 * | 6/2001 | Lopez et al. | 424/547 |
| 6,294,179 B1 | 9/2001 | Lee et al. | |
| 6,526,993 B1 * | 3/2003 | Wagner | 132/321 |
| 6,936,280 B1 * | 8/2005 | Lopez et al. | 424/547 |
| 7,093,599 B2 * | 8/2006 | Chen | 602/1 |
| 7,393,402 B2 * | 7/2008 | Liao | 106/400 |
| 7,461,992 B2 * | 12/2008 | Griffon | 401/266 |
| 7,575,686 B2 * | 8/2009 | Sengupta et al. | 210/617 |
| 7,651,562 B2 * | 1/2010 | Kaupp et al. | 106/400 |
| 2002/0110655 A1 | 8/2002 | Seth | |
| 2002/0155234 A1 * | 10/2002 | Seth | 428/35.2 |
| 2003/0019501 A1 * | 1/2003 | Hirota et al. | 132/73 |
| 2003/0039693 A1 * | 2/2003 | Sandhage | 424/484 |
| 2003/0206933 A1 * | 11/2003 | Schulze zur Wiesche et al. | 424/401 |
| 2004/0005280 A1 * | 1/2004 | Godbout | 424/61 |
| 2004/0161388 A1 * | 8/2004 | Liu et al. | 424/49 |
| 2005/0019588 A1 * | 1/2005 | Berry et al. | 428/424.8 |
| 2005/0226830 A1 * | 10/2005 | Fang | 424/63 |
| 2006/0058714 A1 | 3/2006 | Rhoades | |
| 2006/0088492 A1 * | 4/2006 | Goddinger et al. | 424/70.13 |
| 2006/0112968 A1 * | 6/2006 | Brown et al. | 132/321 |
| 2007/0029302 A1 * | 2/2007 | Russo | 219/222 |
| 2007/0128293 A1 * | 6/2007 | Lopez et al. | 424/547 |
| 2007/0181144 A1 * | 8/2007 | Brown et al. | 132/321 |
| 2008/0087293 A1 * | 4/2008 | Glenn et al. | 132/210 |
| 2008/0189952 A1 * | 8/2008 | Everett et al. | 30/43.4 |
| 2009/0101163 A1 * | 4/2009 | Brunner | 132/320 |
| 2009/0151748 A1 * | 6/2009 | Ridenhour | 134/6 |
| 2009/0159093 A1 * | 6/2009 | Yu | 132/211 |
| 2009/0232580 A1 * | 9/2009 | Castel et al. | 401/41 |
| 2009/0241983 A1 * | 10/2009 | Williams et al. | 132/321 |
| 2010/0015189 A1 * | 1/2010 | Perron et al. | 424/401 |
| 2010/0163071 A1 * | 7/2010 | Everett et al. | 132/223 |
| 2011/0004218 A1 * | 1/2011 | Drai et al. | 606/92 |
| 2011/0104635 A1 * | 5/2011 | Jodaikin et al. | 433/80 |
| 2011/0120487 A1 | 5/2011 | Rollat-Corvol et al. | |

FOREIGN PATENT DOCUMENTS

| | | |
|---|---|---|
| JP | 56131512 A | 10/1981 |
| WO | 2009156668 A2 | 12/2009 |

OTHER PUBLICATIONS www.tigihaircare.com.*

CeraSol Ceramic Coating Applications, http://www.cerasol.com.hk/app_2.html, 2009.

European Search Report mailed on Aug. 8, 2011 in EP11161064.8-1258, filed on Apr. 5, 2010, 2 pages.

* cited by examiner

COATINGS FOR PERSONAL GROOMING APPARATUS CONTAINING CALCIUM CARBONATE DERIVED FROM MOLLUSK SHELLS OR PEARLS

BACKGROUND

The field of this disclosure relates to personal grooming apparatus, such as hair straighteners and curling irons. The apparatus include coatings on the surface thereof that incorporate calcium carbonate derived from the shell of a mollusk or from a mollusk pearl. Other aspects of the present disclosure relate to methods for producing such apparatus, and methods for grooming the hair or skin of an individual.

Consumers have recently developed preferences for manufactured items that are considered natural and/or renewable, or that incorporate natural or renewable components. Such items benefit the environment in that they are continually regenerated and are believed to positively impact the health of the user. These preferences have been particularly observed in consumer choices relating to personal care items, such as items that groom the skin or hair of the user. It conventionally has been difficult to incorporate "natural" components in these devices, as the devices must be made of materials that can withstand high temperatures. Incorporating natural components into hair grooming apparatus, such as curling irons and straighteners, has proven difficult as these apparatus include components that are heated to as much as 250° C.

Calcium carbonate is conventionally used in plastics as a filler and as a flux material in ceramics. In ceramics, calcium carbonate lowers the melting point of the ceramic material and thereby facilitates formation of the ceramic material. Calcium carbonate may be incorporated into ceramic coatings for more efficient kiln operation. Calcium carbonate is conventionally obtained from non-renewable sources such as limestone and/or marble.

A continuing need therefore exists for personal grooming apparatus that contain natural and/or renewable components (e.g., renewable forms of calcium carbonate) and, particularly, for apparatus that incorporate materials that can withstand high temperatures. A need also exists for methods for producing such personal grooming apparatus, and for methods for personal grooming that involve use of apparatus that contain natural components.

SUMMARY

In accordance with the present disclosure, it has been found that calcium carbonate derived or obtained from a natural source, such as mollusk shells or mollusk pearls, may be incorporated into coatings used in personal care apparatus, such as apparatus for grooming the hair or skin. Particularly, a method for mixing the natural calcium carbonate into the coating composition that is used to coat the apparatus has been found which overcomes the problem of carbonate clumping (i.e., heterogeneity in the mixture and the resulting coating).

In one aspect of the present disclosure, a personal grooming apparatus has a substrate and a coating disposed on the substrate. The coating includes calcium carbonate that is derived from the shell of a mollusk or from a mollusk pearl. The coating has a surface for contacting skin or hair during use of the apparatus.

Another aspect of the present disclosure is directed to a method for manufacturing a personal care apparatus for grooming the hair or skin of an individual. In accordance with the method, a coating composition is applied to a substrate of the apparatus. The coating composition includes calcium carbonate and a solvent. The calcium carbonate is derived from the shell of a mollusk or from a mollusk pearl. The coated substrate is heated to vaporize the solvent and form a coating.

A further aspect of the present disclosure is directed to a method for grooming the hair or skin of an individual. In accordance with the method, the hair or skin is contacted with a personal grooming apparatus. The apparatus has a substrate and a coating disposed on the substrate. The coating includes calcium carbonate that is derived from the shell of a mollusk or from a mollusk pearl. The coating has a surface for contacting skin or hair during use of the apparatus.

Various refinements exist of the features noted in relation to the above-mentioned aspects of the present disclosure. Further features may also be incorporated in the above-mentioned aspects of the present disclosure, as well. These refinements and additional features may exist individually or in any combination. For instance, various features discussed below in relation to any of the illustrated embodiments of the present disclosure may be incorporated into any of the above-described aspects of the present disclosure, alone or in any combination.

BRIEF DESCRIPTION OF THE DRAWINGS

Corresponding reference characters indicate corresponding parts throughout the drawings.

DETAILED DESCRIPTION

In accordance with the present disclosure, a personal grooming apparatus includes a coating on a surface thereof that incorporates calcium carbonate derived from mollusk shells or mollusk pearls. For purposes of the present disclosure, "personal grooming apparatus" or "personal care apparatus" includes any item that is used to groom the hair or skin of a user without limitation. Suitable apparatus that groom the hair include, for example, hair straighteners, hair curlers, curling irons, hot rollers (synonymously "hot curlers"), brushes, combs, picks, devices for securing hair (hair ties, berets, etc.), hair clippers and hair razors (which may also be considered a skin product), including the blade or cutting surface thereof. Suitable skin products include the friction-reducing strips or pads incorporated into hair razors, hair razors themselves (e.g., the blade or cutting surface thereof), skin wipes and/or cloths for cleaning of the skin and exfoliating pads. In this regard, personal grooming apparatus other than those listed above may be used without departing from the scope of the present disclosure.

The substrates to which the coating compositions of the present disclosure are applied are generally a surface which contacts the skin or hair during use. For instance, the substrate may be the plates (e.g., aluminum or ceramic) of a hair straightener, the friction reducing pad of a razor, the blade or cutting surface of a razor or the barrel of a curling iron.

Figure 1:
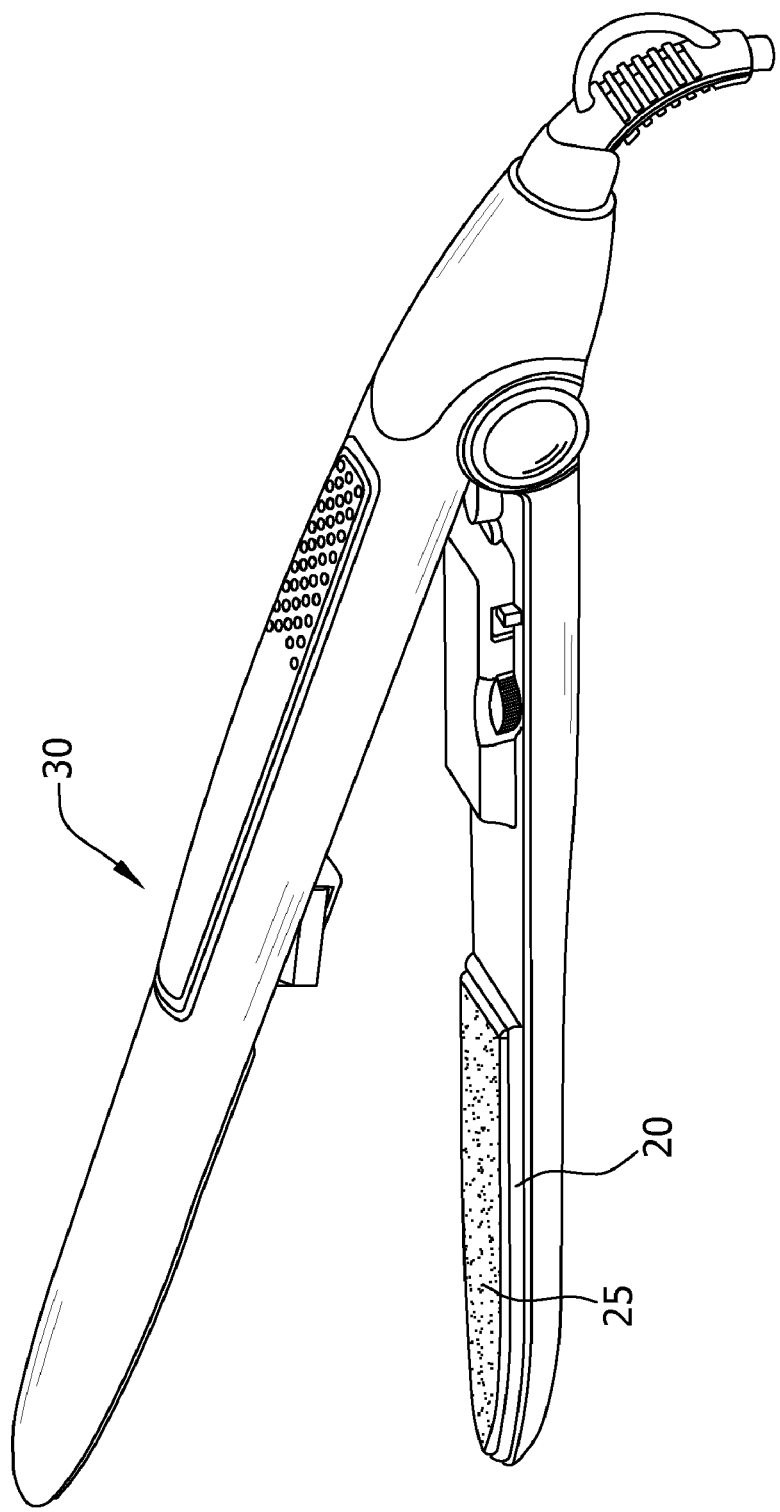
FIG. 1 is a perspective view of a hair straightener with a coating of the present disclosure disposed thereon.
Figure 2:
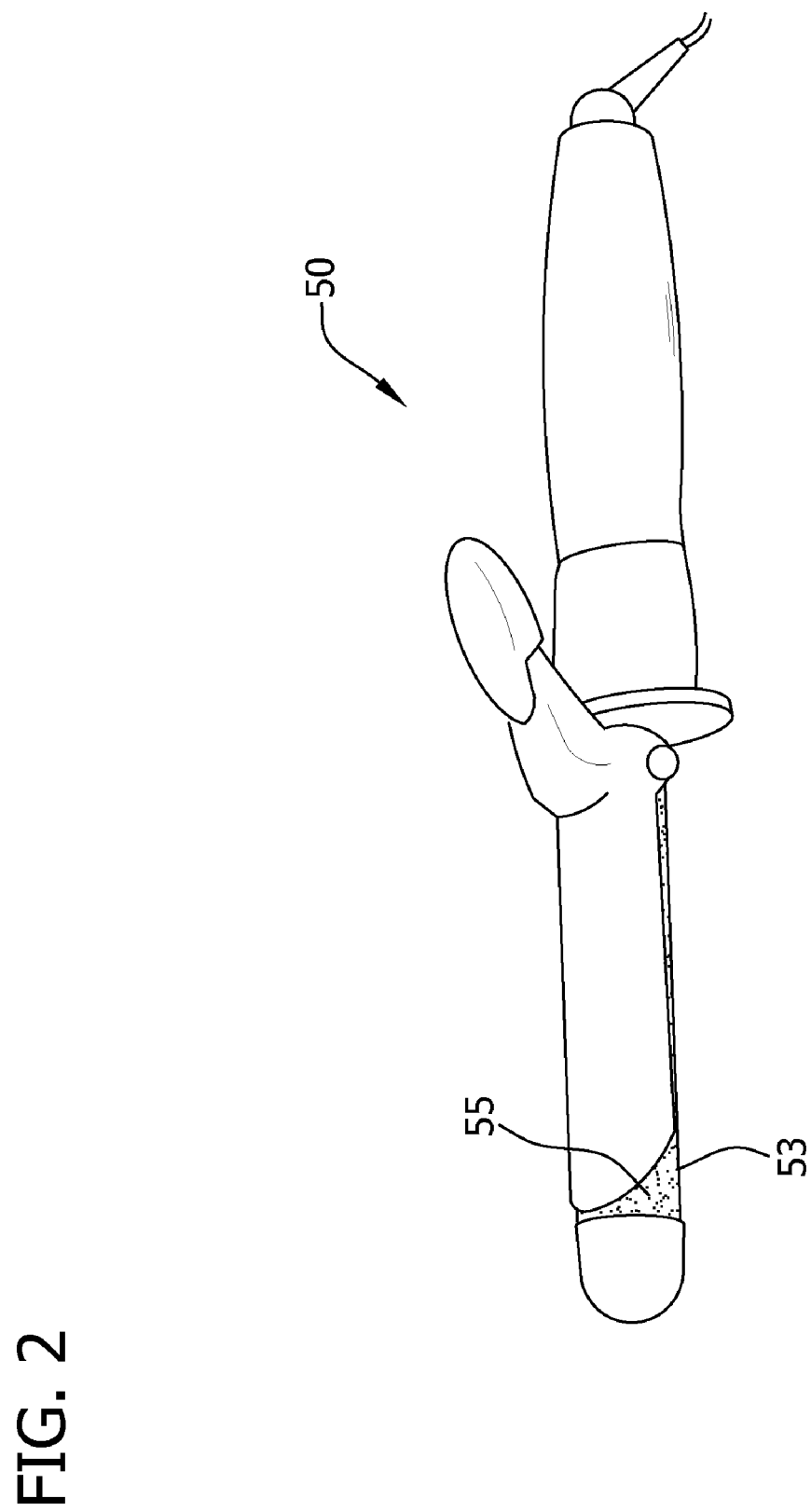
FIG. 2 is a perspective view of a hair curling iron with a coating of the present disclosure on the barrel portion thereof.

Referring now to FIG. 1, a hair straightener 30 which is an exemplary personal care apparatus is shown. The straightener 30 contains a heating plate 20 with a coating 25 of the present disclosure disposed thereon. Another example of a personal grooming apparatus is a hair curling iron 50 which is shown in FIG. 2. The curling iron 50 includes a barrel 53. A coating 55 of the present disclosure may be disposed on the barrel 53.

Figure 3:
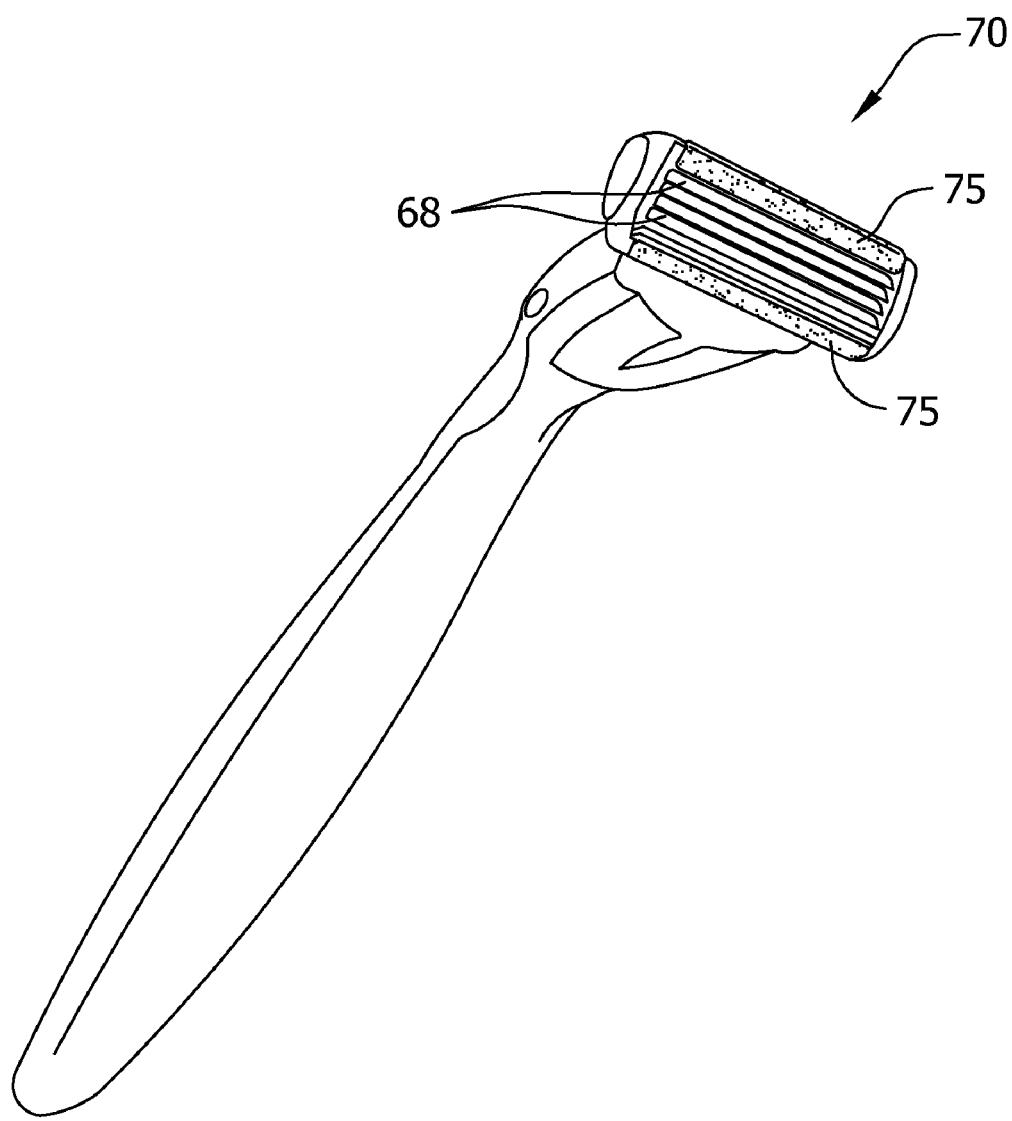
FIG. 3 is a perspective view of a razor with a coating of the present disclosure disposed thereon.

Another example of a personal grooming apparatus is a razor 70 which is shown in FIG. 3. The razor 70 includes one or more razor blades 68. The razor 70 includes one or more friction-reducing pads or strips 75 which are composed of a coating of the present disclosure. Alternatively, or additionally, the blade or cutting surface 68 may also have a coating of the present disclosure applied thereto (not shown).

Figure 4:
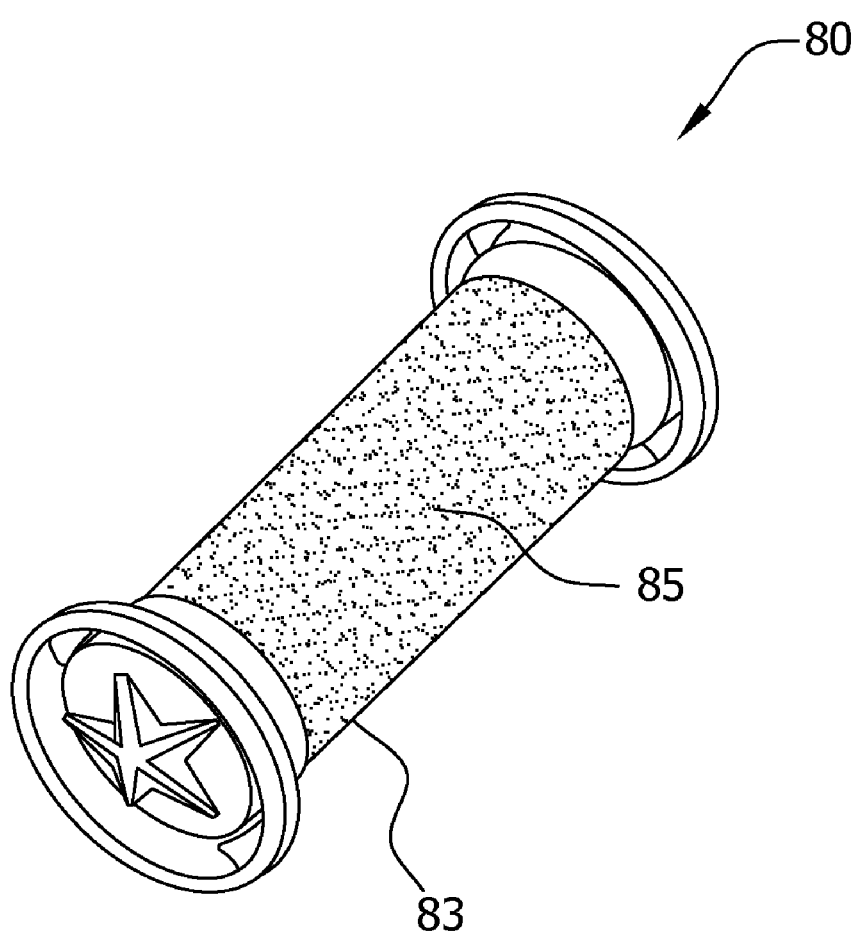
FIG. 4 is a perspective view of a hair hot roller with a coating of the present disclosure on the central tubular portion thereof; and, FIG. 5 is a perspective view of an exfoliating pad coated with a coating of the present disclosure.

Yet another example of a personal care apparatus of the present disclosure is a hot roller 80 which is illustrated in FIG. 4. The hot roller 80 includes a central tubular portion 83. The central tubular portion 83 includes a coating 85 of the present disclosure thereon.

Figure 5:
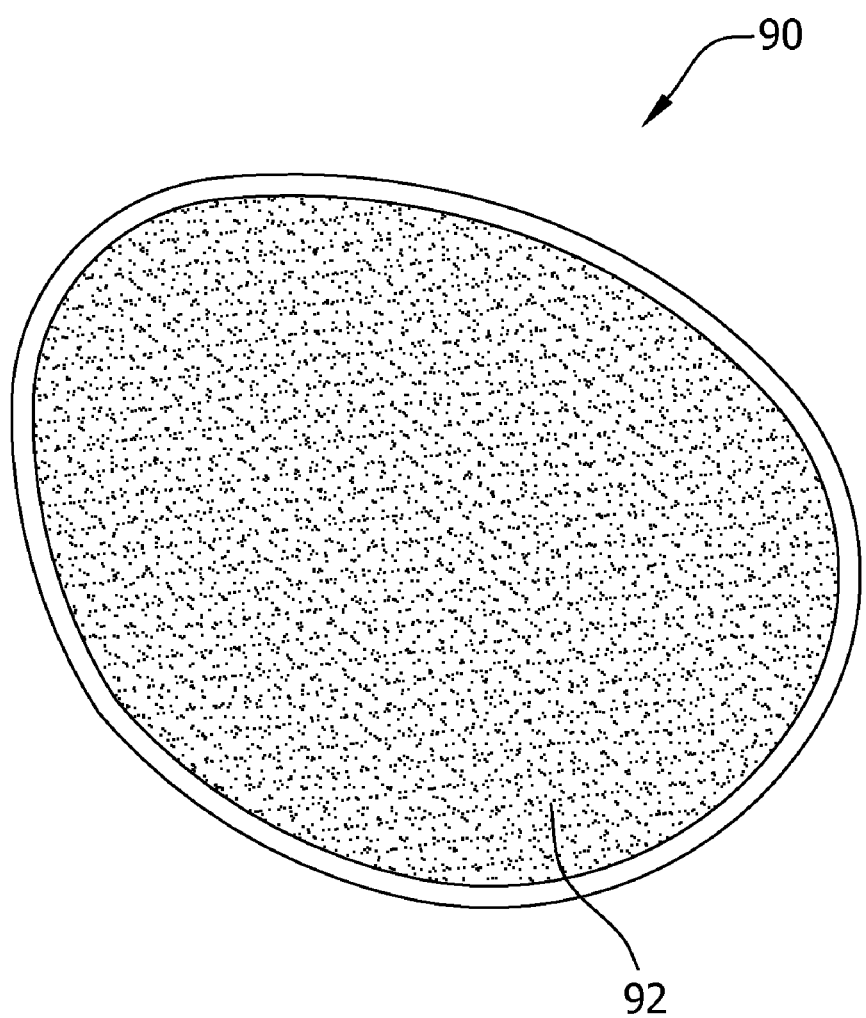

An exfoliating pad 90 which is also an example of a personal grooming apparatus is shown in FIG. 5. The pad 90 includes an exfoliating surface 92 which includes a coating that contains calcium carbonate derived from mollusk shells or pearls at least partially covering the exfoliating surface 92.

Coating Compositions

Generally, calcium carbonate derived or obtained from the shells or pearls of mollusks may be used. For purposes of the present disclosure, use of the phrase "derived from" is meant to indicate that the material was obtained or originated from its source (e.g., mollusks) and is synonymous with "obtained from" and "originating from." Suitable mollusks for use in accordance with the present disclosure include any animals considered to belong to the phylum mollusca and, particularly, mollusks that have a mantle that secretes a shell and/or that produce a pearl. One exemplary mollusk that produces both shells and pearls suitable for use according to the present disclosure is oysters; however, it should be understood that any shell-producing or pearl-producing mollusk may be used without limitation.

The shells of mollusks are diverse and may contain one or more layers with different mineral structures therein. For instance, the shell may contain an inner layer (which is also referred to as an inner "liner" in the art) that is made of nacre or "mother of pearl." Nacre is similar in composition and structure to pearl and is generally iridescent in appearance. Both nacre and pearl may be the source of calcium carbonate used in the coating of the personal care apparatus of the present disclosure.

Nacre and pearl are generally formed of aragonite calcium carbonate crystals. Aragonite crystals may also be included in portions of the shell other than nacre portions. Aragonite as formed in mollusks generally includes calcium carbonate and conchiolin protein (sometimes referred to as "conchin" protein). Conchiolin forms a matrix (e.g., the structural backbone) into which the calcium carbonate crystals are embedded and helps strengthen the aragonite material. In addition to calcium carbonate, the coatings of the grooming apparatus of the present disclosure generally include an amount of conchiolin protein within the coating. Conchiolin is generally not present in calcium carbonate sources other than mollusk sources. For instance, calcium carbonate derived from limestone or marble does not contain conchiolin, despite the fact that marine organisms formed these rocks due to loss of protein structure over large periods of time. The presence of conchiolin in calcium carbonate in the coating compositions of the present disclosure may be detected by any of the methods known by those of skill in the art including, for example, by purification and gel-filtration column chromatography, spectroscopy (e.g., FTIR) or by microscopy methods (e.g., SEM). The amount of conchiolin protein in aragonite-type calcium carbonate (including nacre and pearl) may range from about 0.1 wt % to about 20 wt % with about 10 wt % being typical.

In addition to containing aragonite and conchiolin protein, the shells of mollusks also typically contain calcium carbonate crystallized as calcite. Calcite is often found in the outer layers of mollusk shells. Calcite deposits in the shells of mollusks typically contain less amounts of conchiolin or may completely lack conchiolin.

In this regard it should be understood that the coatings used in personal grooming apparatus may include any combination of aragonite, calcite and conchiolin and these materials may be combined in any number of relative proportions without departing from the scope of the present disclosure. The relative amount of aragonite, calcite and/or conchiolin used in the coating may vary depending on the materials used (e.g., nacre, pearl and/or outer shell) and on the mollusk from which the material is obtained. In some embodiments, the ratio of aragonite to calcite used in the coatings of the present disclosure is from about 10:1 to about 1:10 or from about 1:5 to about 5:1.

Further, the calcium carbonate may be derived from any combination of nacre, the shell outer layers or pearl including use of nacre, outer shell or pearl alone. When an amount of mollusk shell is used in the coating composition, the source of mollusk shell may be pearl-producing mollusks or mollusks that do not produce pearls. It should also be understood that when the coating contains amounts of calcium carbonate derived from pearls, the pearls may be natural pearls, cultured pearls or combinations of these without limitation.

Generally, the mollusk shell and/or pearl are prepared for use by cleaning (e.g., a rinse) and crushing the material to the appropriate particle size. Any of the methods and equipment for cleaning and/or reducing the particle size of calcium carbonate from oyster shells and pearls available to those of skill in the art may be used to reduce the particle size of the calcium carbonate material without limitation. In an exemplary process, pearls and/or mollusk shells may be washed to remove foreign matter and a first particle-size reduction (i.e., crushing operation) may be performed. The crushed material may be washed again to remove soluble material (e.g., heavy metals). The crushed material may be further reduced in size (i.e., to micro-scale or nano-scale particle sizes as described below), dried and, optionally, sterilized. Preparation of the powder may involve mechanical processing (e.g., particle size reduction by use of ultrasonic air) or involve chemical or enzymatic methods. The cleaning and/or particle size reduction steps (including the selection and order thereof) and the process parameters (i.e., cleaning times, desired particle sizes and the like) may vary and may be readily determined by those of skill in the art. The cleaning and particle size reduction steps recited herein should not be considered in a limiting sense as the particular process employed may vary as appreciated by those of skill in the art.

In some embodiments, the particle size of the calcium carbonate material is controlled to be less than the thickness of the calcium carbonate containing coating. This generally allows the cured coating to be smooth to the touch which is desirable in many personal care apparatus. For instance, the average particle size of the calcium carbonate particles may be reduced to less than about 75% of the thickness of the coating layer that comprises the calcium carbonate and, in other embodiments, less than about 50%, less than about 25% or from about 10% to about 50% of the coating layer thickness. Typically the average particle size of the calcium carbonate will be less than about 50 μm or even less than about 20 μm, less then about 10 μm or less than about 5 μm (e.g., from about 0.1 μm to about 75 μm or from about 0.1 μm to about 20 μm).

It has been found that by reducing the particle size of the calcium carbonate (or a portion of the calcium carbonate) derived from mollusk shells or mollusk pearls, the material better homogenizes in the liquid coating composition and the coating as cured. Generally, conventional mineral deposits (e.g., limestone) have been found to readily homogenize and produce a more uniform coating and, as a result, the particle size distribution of the calcium carbonate is not controlled. Without being bound to any particular theory, it is believed that protein within the mollusk-derived calcium carbonate causes clumping during mixing. To prevent this clumping and to produce a uniform coating, in some embodiments, a portion of the calcium carbonate is reduced in size to a "nano-scale" particle size (i.e., particles with a particle size of less than about 100 nm). For instance, the average particle size of these nano-scale particles may be less than about 100 nm, less than about 50 nm or even less than about 10 nm (e.g., from about 1 nm to about 100 nm or from about 10 nm to 100 nm). In certain embodiments of the present disclosure, at least about 99% of the nano-scale particles have a particle size of at least about 5 nm (e.g., from 5 nm to about 100 nm). Optionally, at least about 75% of the nano-scale particles have a particle size of from about 40 nm to about 80 nm.

The calcium carbonate derived from mollusk shells or pearls may contain particles of a size other than nano-sized particles. In such embodiments, it is preferred that the weight ratio of nano-scale particles to other particles (e.g., micro-scale particles) is at least about 1:20 or even at least about 1:10 (e.g., from about 1:1 to about 1:20 or from about 1:2 to about 1:10). Particles other than nano-scale particles include micro-scale particles (e.g., particles with a particle size of at least about 100 nm and less than about 1000 nm). For instance, the micro-scale particles may have a particle size less than about 750 nm, less than about 500 nm, less than about 250 nm or even less than about 150 nm (e.g., from about 100 nm to about 1000 nm or from about 500 nm to about 1000 nm). Micro-scale particles, unlike nano-scale particles, may be seen at the surface of the coating and help give the coating an iridescent appearance.

In regard to conchiolin protein, both nano-scale and micro-scale calcium carbonate may have conchiolin embedded within the calcium carbonate particles. The conchiolin protein generally does not separate from the calcium carbonate as distinct particles during particle size reduction.

The personal care apparatus of the present disclosure are generally prepared by applying a coating composition to a targeted surface of the apparatus. In this regard it should be understood that, as used herein, "coating compositions" or simply "compositions" refer to the composition that is applied to the substrate and not the coating itself which forms after additional processing steps (e.g., vaporization of solvent, heating, curing, sintering and the like). As used herein, the term "coating" refers to the material on the surface of the substrate after all processing steps are complete and is not meant to include any solvent and/or carrier that evaporates from the coating composition.

For instance, in certain embodiments the coating composition contains a volatile carrier or solvent such as an alcohol that may be evaporated from the composition to form the "coating." The percent inclusion of components of the "coating composition" as described herein refer to the material applied to the substrate of the personal care apparatus; whereas, percent inclusion of the components of the "coating" (described below under the section entitled "Calcium Carbonate Coatings") refer to the solid material covering a portion of the substrate after all processing steps are completed. Unless described otherwise, listed percentages are given as the percentage of the entire composition or entire coating including the component or components being described.

In some embodiments of the present disclosure, the coating composition that is applied to the substrate contains at least about 0.01 wt % calcium carbonate derived from shells of a mollusk or from a mollusk pearl. In other embodiments, the coating composition contains at least about 0.05 wt %, at least about 0.1 wt %, at least about 0.3 wt %, at least about 0.5 wt % or from about 0.01 wt % to about 5 wt %, from about 0.01 wt % to about 3 wt % or from about 0.05 wt % to about 1 wt % calcium carbonate derived from the shell of a mollusk or from a mollusk pearl.

The coating composition used to apply the calcium carbonate coating of the present disclosure may include a number of components other than calcium carbonate. For instance, the coating composition may contain an amount of metal oxides (i.e., ceramics) such as, for example, silicon oxide or titanium oxide. The ceramics give the coating its basic structure and help ensure that the coating is uniform over the substrate of the personal care apparatus. Suitable ceramics include, for example, silicon dioxide, titanium dioxide, zirconium oxide and alumina oxide. The amount of ceramic materials in the coating composition should not exceed an amount at which the coating composition is not sufficiently flowable to allow the coating composition to be applied to the substrate. The amount of ceramics in the coating composition may be at least about 5 wt %, at least about 50 wt % or even at least about 70 wt % (e.g., from about 30 wt % to about 90 wt %, from about 40 wt % to about 80 wt % or from about 50 wt % to about 80 wt %).

In certain embodiments, the coating composition does not contain any amount of ceramics but rather only calcium carbonate and other additives. Alternatively or in addition, the coating composition may contain an amount of polymer resin such as a fluoropolymer (e.g., polytetrafluoroethylene, perfluoroalkoxy, fluorinated ethylene propylene and mixtures thereof). The fluoropolymers may be silicone modified (i.e., a co-polymer with silicone functionality may be incorporated into the fluoropolymer) which allows the coating to be more durable and to better withstand temperature extremes. When fluoropolymer resins are used, the amount of fluoropolymer resin that is used in the coating composition may be at least about 20 wt %, at least about 40 wt % or at least about 50 wt % (e.g., from about 20 wt % to about 85 wt %, from about 40 wt % to about 85 wt % or from about 50 wt % to about 70 wt %).

The coating compositions of the present disclosure may also contain an amount of tourmaline (e.g., from about 0.01 wt % to about 10 wt %). It is believed that tourmaline produces negative ions when heated which reduces hair static. Other functional components may be included in the coating composition without departing from the scope of the present disclosure. For instance, the coating composition may optionally include one or more additives such as colorants, binders, dispersants, sintering aids, plasticizers, antimicrobials (e.g., nano silver or nano titanium dioxide), hardeners (e.g., nano diamond) and the like.

An amount of nano-sized titanium dioxide may be included into the coating composition (e.g., from about 0.05 wt % to about 5 wt %, from about 0.05 wt % to about 1 wt % or from about 0.1 wt % to about 0.5 wt %). The nano-sized titanium dioxide may act as an anti-bacterial agent upon absorption of light. When nano-sized titanium dioxide is used, it is preferred that the coating be somewhat porous to allow light to penetrate the coating and contact the nano-sized titanium dioxide.

The coating composition may include one or more coloring agents (i.e., "colorants") that modify the appearance of the coating. Examples of such colorants include mica powder and various color pigments. The amount of colorants in the coating composition may range from about 0.01 wt % to about 20 wt % (e.g., from about 0.5 wt % to about 15 wt % or from about 3 wt % to about 15 wt %).

Generally, the binder alters the rheology of the coating composition and maintains the distribution of particles in the solution throughout application and curing. Suitable binders for use in the coating composition include polyvinyl butyral which may be present in an amount of at least about 0.5 wt % (e.g., 0.5 wt % to about 20 wt % or from about 1 wt % to about 10 wt %).

The coating composition may include a dispersant that acts to prevent the particulate from settling prior to application of the coating composition to the substrate. The dispersant may be present in an amount of at least about 0.05 wt % (e.g., from about 0.05 wt % to about 10 wt % or from about 0.1 wt % to about 5 wt %). One suitable dispersant for use in the composition is a methyloxirane polymer.

A plasticizer may also be included in the composition. The plasticizer may be chosen to allow the coating composition to dry without cracking. The plasticizer may be present in an amount of at least about 0.5 wt % (e.g., 0.5 wt % to about 20 wt % or from about 1 wt % to about 10 wt %). One suitable plasticizer is polyethylene glycol.

The coating composition generally includes a medium in which the coating components are applied to the substrate. For instance, the medium may be a solvent in which the calcium carbonate at least partially dissolves. In this regard, it should be understood that while the term "solvent" is used herein, portions of the calcium carbonate as well as the ceramics remain substantially in particulate form throughout the solvent. Thus, the solvent may also be referred to as a "diluent" in which the particulate components are suspended. For purposes of the present disclosure, the terms "medium," "diluent," and "solvent" may be used interchangeably and are not meant to limit embodiments of the present disclosure to compositions wherein one or more components do or do not dissolve.

Suitable solvents include water and/or organic compounds. Suitable organic compounds include, for example, C1 to C10 alcohols, methyl ethyl ketone, acetone, petroleum distillates and combinations of these compounds. The amount of solvent may vary according to the desired flowability of the coating composition. In some embodiments of the present disclosure, the coating composition contains at least about 5 wt % solvent (or solvents when more than one solvent is used) and, in other embodiments, at least about 10 wt % or even about 20 wt % solvent (e.g., from about 5 wt % to about 50 wt % or from about 5 wt % to about 30 wt % solvent). Preferably the solvent vaporizes readily during any drying steps. The composition may include more than one solvent with the total weight fraction of solvents in the composition being as described above. In certain embodiments, both water and a C1 to C10 alcohol (e.g., ethanol) are included as solvents. The weight ratio of water to C1 to C10 alcohol may range from 1:2 to 10:1 and, in other embodiments, from about 1:1 to 5:1.

In one or more embodiments of the present disclosure, the coating composition containing calcium carbonate derived from mollusk shells or oysters is applied to a base coating that is disposed on the substrate. The base coating may contain ceramics (e.g., silica, titania, zirconia, and chromic (III) oxide) and other additives such as barium sulfate that improve the rheological properties of the coating. The base coating optionally does not contain calcium carbonate as the calcium carbonate coating is disposed on its surface. In this regard, it should be noted that when at least two coating compositions are applied to the substrate, other arrangements of coating layers may be used including arrangements in which more than two layers are used or in which the calcium carbonate coating is not disposed at the surface of the substrate without departing from the scope of the present disclosure.

In embodiments wherein a base coating composition is applied to the substrate prior to application of the calcium carbonate top coating composition, the base coating composition may contain at least about 0.5 wt % barium sulfate or even at least about 1 wt % barium sulfate (e.g., from about 0.5 wt % to about 15 wt % or from about 1 wt % to about 8 wt %). The amount of ceramics in the base coating composition may be at least about 30 wt %, at least about 50 wt % or even at least about 70 wt % (e.g., from about 30 wt % to about 90 wt %, from about 40 wt % to about 80 wt % or from about 50 wt % to about 80 wt %). The base coating composition may include a solvent such as one or more C1 to C10 alcohols, methyl ethyl ketone, acetone, petroleum distillates and combinations of these compounds. In some embodiments of the present disclosure, the base coating composition contains at least about 5 wt % solvent (or solvents when more than one solvent is used) and, in other embodiments, at least about 10 wt % or even about 20 wt % solvent (e.g., from about 5 wt % to about 50 wt % or from about 5 wt % to about 30 wt % solvent).

The base coating composition may also contain binders, dispersants, sintering aids, plasticizers and the like as described above in regard to the calcium carbonate containing coating.

Methods for Applying the Coating Compositions of the Present Disclosure

The substrate materials to which the coating compositions of the present disclosure are applied may be subjected to one or more surface preparation procedures before the coating composition is applied. For instance, the surface may be cleaned by rinsing in water or in a dilute cleaning solution that is compatible with the substrate (e.g., a solution of trichloroethylene or other degreasing solution). The surface of the substrate may also be smoothed by conventional surface roughness reduction techniques (e.g., sand or alumina blasting) to remove any surface roughness that may extend through the coating. Sand or alumina-blasting may also be performed to assist in adhesion of the coating composition to the substrate.

The coating composition may generally be applied to the substrate by any of the methods known to those of ordinary skill in the art. Suitable methods include spray coating, immersion, brushing and powder coating techniques. Conventional spray coating methods may be used including air, air-assisted, airless and electrostatic atomization. Air Atomization may be performed under high-volume, low pressure conditions such as pressures below about 35 MPa. It should be noted that when powder coating techniques are used, the coating composition does not contain solvents and no curing step is performed. Generally, the coating composition is a powder that has the same chemical composition of the coating itself. Powder coating techniques known to those of skill in the art may be used in accordance with the present disclosure. The coating composition may be subjected to a filtering operation (e.g., screening) before application of the coating composition so as to remove undesirable larger particles (e.g., particles greater than about 30 μm or greater than about 75 μm in size).

In methods other than powder coating techniques, the coating composition is generally cured to evaporate liquid solvents and diluents and to form and harden the coating. In some embodiments, the coating composition is heated to a temperature of at least about 140° C. and, in other embodiments, to a temperature of at least about 200° C., at least about 300° C., at least about 400° C. (e.g., from about 140° C. to about 500° C. or from about 180° C. to about 300° C.). Other temperatures may be used without departing from the scope of the present disclosure such as room temperature air drying and temperatures at which the coating is sintered (e.g., above about 1000° C.). Curing typically may be completed in from about ten minutes to about two hours depending on the amount of solvent and the temperatures used to cure.

As described above, the calcium carbonate containing coating may be applied to the surface of a base coating that is disposed on the surface of the substrate. The base coating may be formed by the methods described above relating to application of the calcium carbonate containing coating. In some embodiments, the base coating is formed by spraying a base coating composition to the substrate and curing the composition (e.g., to at least about 140° C.). The base coating may be cured before application; however, in some embodiments of the present disclosure, the top coating is applied to the base coating before any curing operations and the base coating and top coating compositions are cured at once (i.e., wet-on-wet coating).

In embodiments wherein a single coating is applied to the substrate of the personal grooming apparatus (i.e., when a base coating is not used), the coating composition may be applied such that the coating as cured has a thickness of at least about 5 μm, at least about 30 μm, at least about 50 μm, or at least about 150 μm (e.g., from about 5 μm to about 500 μm, from about 5 μm to about 250 μm, from about 5 μm to about 100 μm or from about 50 μm to about 70 μm).

When multiple coatings are applied (e.g., a base coat applied to the surface of the substrate with a calcium carbonate coating applied thereto), the total thickness of the coatings applied to the substrate are generally within the ranges described above. In various embodiments, the calcium containing layer (which is typically the surface layer) may have a thickness of less than about 100 μm, less than about 50 μm, or less than about 20 μm (e.g., from about 3 μm to about 100 μm, from about 3 μm to about 20 μm or from about 10 μm to about 20 μm). In some embodiments, the base layer is thicker than the calcium carbonate containing layer (e.g., from about 5 μm to about 50 μm thicker). The thickness of the base layer may be less than about 150 μm, less than about 75 μm, less than about 40 μm or less than about 30 μm (e.g., from about 10 μm to about 150 μm, from about 3 nm to about 30 μm or from about 15 μm to about 30 μm). In this regard, other thicknesses may be used without departing from the scope of the present disclosure and the recited ranges should not be viewed in a limiting sense.

Calcium Carbonate Coatings

The coatings of the personal care apparatus of the present disclosure generally include the components of the coating composition described above excluding any amount of material that was removed during processing (e.g., evaporated solvent). In certain embodiments, the coating contains calcium carbonate derived from mollusk shells or pearls, one or more ceramics and, optionally tourmaline. Generally, the coating as applied (i.e., after all processing steps including curing have been completed) contains at least about 0.01 wt % calcium carbonate derived from the shell of a mollusk or from a mollusk pearl. In other embodiments, the coating contains at least about 0.05 wt %, at least about 0.1 wt %, at least about 0.3 wt %, at least about 0.5 wt % or from about 0.01 wt % to about 5 wt %, from about 0.01 wt % to about 3 wt % or from about 0.05 wt % to about 1 wt % calcium carbonate derived from the shell of a mollusk or from a mollusk pearl. In this regard, it should be noted that the percent inclusions recited above are expressed as a percentage weight of the calcium carbonate containing coating and material from any other base coatings and/or top coatings are excluded in the calculation of the percent inclusion.

In view that the calcium carbonate used in the coatings of the present disclosure are derived from a mollusk source (e.g., mollusk shell or pearl), the calcium carbonate containing coating typically contains amounts of conchiolin protein. For instance, the calcium carbonate containing coating may contain at least about 0.001 wt % conchiolin. In other embodiments, the coating contains at least about 0.005 wt %, at least about 0.01 wt %, at least about 0.03 wt %, at least about 0.05 wt % or from about 0.001 wt % to about 0.5 wt %, from about 0.001 wt % to about 0.3 wt % or from about 0.005 wt % to about 0.1 wt % conchiolin protein.

It should be noted that while the coatings of the present disclosure (or the calcium carbonate containing coating when multi-layer coatings are used) have been described as containing calcium carbonate derived from mollusk shells or mollusk pearls, the coating may also contain amounts of calcium carbonate that is not derived from mollusk shells or pearls (e.g., limestone derived calcium carbonate). In this regard, of the total amount of calcium carbonate in the coating (or calcium carbonate coating when multi-layers are used) the amount that is derived from mollusk shells or pearls may be at least about 1 wt % of the total calcium carbonate in the coating or at least about 5 wt %, at least about 20 wt %, at least about 50 wt %, at least about 90 wt %, at least about 99 wt % or even at least about 99.9 wt % of the total calcium carbonate in the coating. In some embodiments, all of the calcium carbonate in the coating is derived from mollusk shells or pearls (i.e., contains amounts of conchiolin) and none of it is derived from other sources (e.g., limestone). Stated differently, the calcium carbonate present in the coating may consist of or, alternatively, consist essentially of calcium carbonate derived from mollusk shells or pearls (e.g., no more than about 1% of the calcium carbonate is derived from other sources).

The coating may also include ceramics material (e.g., silica, titania, alumina and the like) after all processing steps are complete. The amount of ceramics in the coating may be at least about 40 wt %, at least about 70 wt % or even at least about 90 wt % (e.g., from about 40 wt % to about 99 wt %, from about 70 wt % to about 99 wt % or from about 90 wt % to about 99 wt %). In some embodiments, the coating does not contain an amount of ceramics. When fluoropolymer resins are included in the coating, the amount of fluoropolymer resin may be at least about 20 wt % of the coating, at least about 40 wt % or at least about 50 wt % (e.g., from about 20 wt % to about 85 wt %, from about 40 wt % to about 85 wt % or from about 50 wt % to about 70 wt %). The coating may also contain residual binders, dispersants, plasticizers, and sintering agents that were not removed during processing (e.g., curing).

In some embodiments, the coating may be adapted such that during use of the personal grooming apparatus, an amount of calcium carbonate separates from the coating and attaches to the hair or skin of the user. The calcium carbonate may modify the pH of the skin or hair which may positively affect the appearance or health of the skin or hair. Generally, only a small amount of calcium carbonate attaches to the skin or hair of the user which allows the personal grooming apparatus to repeatedly release and deposit calcium carbonate on the hair or skin of the user. Any of the means for adapting the coating such that it deposits an amount of calcium carbonate may be used without departing from the scope of the present disclosure.

EXAMPLES

Example 1

Preparation of a Two-Layer Coating with the Top Coat Containing Calcium Carbonate Derived from Mollusk Shells or Pearls on a Hair Straightener Two coating compositions were prepared to form a base coating and a calcium carbonate top coating on aluminum plates of a hair straightener. The mollusk derived calcium carbonate used in the top coating composition contained both nano-scale and micro-scale particles. The calcium carbonate was derived from mollusk pearls and/or shells. The coating compositions were filtered in a 200-400 mesh screen (74 μm-37 μm spacing).

After mixing, the top coating composition appeared well-mixed and homogeneous. The components of both coating compositions and their weight inclusion are shown in Tables 1 and 2 below.

TABLE 1

Composition of the Base Coating

| Component | Weight Inclusion (%) |
|---|---|
| $SiO_2$ | 60.5 |
| $H_2O$ | 23.8 |
| $BaSO_4$ | 5.0 |
| $TiO_2$ | 5.8 |
| $ZrO_2$ | 0.9 |
| $Cr_2O_3$ | 4.0 |

TABLE 2

Composition of the Top Coating

| Component | Weight Inclusion (%) |
|---|---|
| $SiO_2$ | 72.5 |
| $H_2O$ | 16.6 |
| Micro-Scale $CaCO_3$ | 0.5 |
| Nano-Scale $CaCO_3$ | 0.1 |
| $TiO_2$ (Nano-scale) | 0.3 |
| Tourmaline | 1.0 |
| Alcohol | 9.0 |

The plates of the hair straightener were cleaned and sandblasted before application of the coating compositions. The base coating composition was then applied to the plates of the hair straightener by spraying. After the base coating composition was applied, the top coating composition containing the calcium carbonate derived from mollusk pearls was applied to the surface of the base coating compositions by spraying. After application of the base coating composition and the top coating composition, the coating compositions were both cured at a temperature of 180° C. for 30 minutes. After curing, the base coating had a thickness of about 30 μm and the top coating had a thickness of about 10 μm. The top coating appeared iridescent and was smooth to the touch.

Example 2

Preparation of a Two-Layer Coating with the Top Coat Containing Calcium Carbonate Derived from Mollusk Shells or Pearls on a Curling Iron The coating procedure of Example 1 was repeated by coating the barrel of a curling iron. The barrel of the curling iron was made of aluminum. After application and curing of the coating compositions, the top coating appeared iridescent and was smooth to the touch.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatus and methods without departing from the scope of the disclosure, it is intended that all matter contained in the above description and shown in the accompanying figures shall be interpreted as illustrative and not in a limiting sense.

What is claimed is:

1. A personal grooming apparatus, the apparatus having:
   a substrate;
   a coating disposed on the substrate, the coating comprising calcium carbonate and having a thickness of from about 3 μm to about 100 μm, the calcium carbonate being derived from the shell of a mollusk or from a mollusk pearl, the calcium carbonate containing coating having a surface for contacting skin or hair during use of the apparatus; and,
   a base coating disposed between the substrate and the calcium carbonate containing coating, the base coating having a thickness of from about 10 μm to about 30 μm.

2. The personal grooming apparatus as set forth in claim 1 wherein the calcium carbonate containing coating comprises conchiolin protein.

3. The personal grooming apparatus as set forth in claim 2 wherein the conchiolin forms a matrix in which calcium carbonate is embedded.

4. The personal grooming apparatus as set forth in claim 2 wherein the calcium carbonate containing coating comprises at least about 0.001 wt % conchiolin.

5. The personal grooming apparatus as set forth in claim 1 wherein the calcium carbonate containing coating comprises nacre.

6. The personal grooming apparatus as set forth in claim 1 wherein the calcium carbonate containing coating comprises at least about 0.01 wt % calcium carbonate derived from the shell of a mollusk or from a mollusk pearl.

7. The personal grooming apparatus as set forth in claim 1 wherein the calcium carbonate containing coating comprises a component selected from one or more metal oxides, tourmaline and mixtures thereof.

8. The personal grooming apparatus as set forth in claim 1 wherein the base coating does not comprise calcium carbonate.

9. The personal grooming apparatus as set forth in claim 1 wherein the thickness of the calcium carbonate containing coating is from about 5 μm to about 25 μm.

10. The personal grooming apparatus as set forth in claim 1 wherein the average particle size of the calcium carbonate is less than about 50 μm.

11. The personal grooming apparatus as set forth in claim 1 wherein the calcium carbonate contains both nano-scale and micro-scale particles.

12. The personal grooming apparatus as set forth in claim 11 wherein at least about 99% of the total nano-scale particles have a particle size of at least about 5 nm and at least about 75% of the nano-scale particles have a particle size of from about 40 nm to about 80 nm.

13. The personal grooming apparatus as set forth in claim 1 wherein the mollusk is an oyster.

14. The personal grooming apparatus as set forth in claim 1 wherein the apparatus is selected from the group consisting of a hair straightener, hair curler, curling iron, hot roller, a device for securing hair, shaver, clipper, friction-reducing strips or pads, brush, comb, wipe, cloth and exfoliating pads.

15. The personal grooming apparatus as set forth in claim 1 wherein the thickness of the calcium carbonate containing coating is from about 5 μm to about 100 μm.

16. A personal grooming apparatus, the apparatus having a substrate and a coating disposed on the substrate, the coating comprising calcium carbonate, the calcium carbonate being derived from the shell of a mollusk or from a mollusk pearl, the calcium carbonate containing coating having a surface for contacting skin or hair during use of the apparatus, the calcium carbonate comprising both nano-scale and micro-scale particles with at least about 99% of the total nano-scale particles having a particle size of at least about 5 nm and at least about 75% of the nano-scale particles having a particle size of from about 40 nm to about 80 nm.

17. The personal grooming apparatus as set forth in claim 16 wherein the calcium carbonate containing coating comprises conchiolin protein.

18. The personal grooming apparatus as set forth in claim 17 wherein the conchiolin forms a matrix in which calcium carbonate is embedded.

19. The personal grooming apparatus as set forth in claim 17 wherein the calcium carbonate containing coating comprises at least about 0.001 wt % conchiolin.

20. The personal grooming apparatus as set forth in claim 16 wherein the calcium carbonate containing coating comprises nacre.

21. The personal grooming apparatus as set forth in claim 16 wherein the calcium carbonate containing coating comprises at least about 0.01 wt % calcium carbonate derived from the shell of a mollusk or from a mollusk pearl.

22. The personal grooming apparatus as set forth in claim 16 wherein the calcium carbonate containing coating comprises a component selected from one or more metal oxides, tourmaline and mixtures thereof.

23. The personal grooming apparatus as set forth in claim 16 further comprising a base coating disposed between the substrate and the calcium carbonate containing coating.

24. The personal grooming apparatus as set forth in claim 23 wherein the base coating does not comprise calcium carbonate.

25. The personal grooming apparatus as set forth in claim 16 wherein the thickness of the calcium carbonate containing coating is from about 3 μm to about 100 μm.

26. The personal grooming apparatus as set forth in claim 16 wherein the thickness of the calcium carbonate containing coating is from about 5 μm to about 100 μm.

27. The personal grooming apparatus as set forth in claim 16 wherein the average particle size of the calcium carbonate is less than about 50 μm.

28. The personal grooming apparatus as set forth in claim 16 wherein the mollusk is an oyster.

29. The personal grooming apparatus as set forth in claim 16 wherein the apparatus is selected from the group consisting of a hair straightener, hair curler, curling iron, hot roller, a device for securing hair, shaver, clipper, friction-reducing strips or pads, brush, comb, wipe, cloth and exfoliating pads.

* * * * *